(12) United States Patent
Cook et al.

(10) Patent No.: US 12,303,887 B2
(45) Date of Patent: May 20, 2025

(54) METHODS AND APPARATUS FOR MANUFACTURING A MICROFLUIDIC ARRANGEMENT, AND A MICROFLUIDIC ARRANGEMENT

(71) Applicant: OXFORD UNIVERSITY INNOVATION LIMITED, Oxford (GB)

(72) Inventors: Peter Richard Cook, Oxford (GB); Alexander Feuerborn, Oxford (GB); Edmond Walsh, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 1696 days.

(21) Appl. No.: 16/326,129

(22) PCT Filed: Apr. 18, 2017

(86) PCT No.: PCT/GB2017/051065
§ 371 (c)(1),
(2) Date: Feb. 15, 2019

(87) PCT Pub. No.: WO2018/033692
PCT Pub. Date: Feb. 22, 2018

(65) Prior Publication Data
US 2019/0176148 A1     Jun. 13, 2019

(30) Foreign Application Priority Data

Aug. 18, 2016 (GB) ...................... 1614139
Aug. 18, 2016 (GB) ...................... 1614146
(Continued)

(51) Int. Cl.
*B01L 3/00* (2006.01)
*C12M 1/00* (2006.01)
*C12M 3/06* (2006.01)

(52) U.S. Cl.
CPC ... *B01L 3/502707* (2013.01); *B01L 3/502715* (2013.01); *B01L 3/50273* (2013.01);
(Continued)

(58) Field of Classification Search
None
See application file for complete search history.

(56) References Cited

U.S. PATENT DOCUMENTS 6,664,044 B1   12/2003   Sato
7,189,580 B2   3/2007    Beebe et al.
(Continued)

FOREIGN PATENT DOCUMENTS

CN   1337580 A   2/2002
CN   1767899 A   5/2006
(Continued)

OTHER PUBLICATIONS

Barnes, et al., "Chapter 2: Capillarity and the mechanics of surfaces of Interfacial Science: An introduction," Interfacial Science, 2011, pp. 10-42.
(Continued)

*Primary Examiner* — Jennifer Wecker
*Assistant Examiner* — Bryan Kilpatrick
(74) *Attorney, Agent, or Firm* — Foley & Lardner LLP

(57) ABSTRACT

Methods and apparatus for manufacturing a microfluidic arrangement are disclosed. In one arrangement a continuous body of a first liquid is provided in direct contact with a substrate. A second liquid is provided in direct contact with the first liquid and covering the first liquid. The first liquid is in direct contact exclusively with the second liquid and the
(Continued)

substrate. The second liquid is forced through the first liquid and into contact with the substrate in selected regions of the substrate in order to divide the continuous body of the first liquid into a plurality of sub-bodies of the first liquid that are separated from each other by the second liquid. The first liquid is immiscible with the second liquid. Surface tension stably holds the plurality of sub-bodies of the first liquid separated from each other by the second liquid.

22 Claims, 10 Drawing Sheets

(30) Foreign Application Priority Data

| Aug. 18, 2016 | (GB) | ................................. | 1614150 |
| Aug. 18, 2016 | (GB) | ................................. | 1614153 |
| Aug. 18, 2016 | (GB) | ................................. | 1614157 |
| Oct. 14, 2016 | (WO) | ............ | PCT/GB2016/053204 |

(52) U.S. Cl.
CPC ....... *B01L 3/502784* (2013.01); *B01L 3/5088* (2013.01); *C12M 23/16* (2013.01); *C12M 29/14* (2013.01); *B01L 2200/0673* (2013.01); *B01L 2200/0694* (2013.01); *B01L 2200/12* (2013.01); *B01L 2300/047* (2013.01); *B01L 2300/06* (2013.01); *B01L 2300/0816* (2013.01); *B01L 2300/0867* (2013.01); *B01L 2300/089* (2013.01); *B01L 2400/0463* (2013.01); *B01L 2400/0469* (2013.01); *B01L 2400/0475* (2013.01); *B01L 2400/0487* (2013.01); *B01L 2400/088* (2013.01)

(56) References Cited

U.S. PATENT DOCUMENTS

| 8,053,249 | B2 | 11/2011 | Beebe et al. |
| 8,168,133 | B2 | 5/2012 | Beebe et al. |
| 8,298,833 | B2 | 10/2012 | Davies et al. |
| 8,361,782 | B2 | 1/2013 | Pugia et al. |
| 8,652,852 | B2 | 2/2014 | Beebe et al. |
| 8,985,547 | B2 | 3/2015 | Weibel et al. |
| 9,296,241 | B1 | 3/2016 | Ihnen et al. |
| 9,707,560 | B2 | 7/2017 | Muelleder et al. |
| 10,159,979 | B2 | 12/2018 | Foulds et al. |
| 2002/0176072 | A1 | 11/2002 | Beseki et al. |
| 2003/0213905 | A1 | 11/2003 | Lennon et al. |
| 2003/0224528 | A1 | 12/2003 | Chiou et al. |
| 2005/0272159 | A1* | 12/2005 | Ismagilov ........... B01F 33/3021 |
| | | | 436/34 |
| 2006/0166233 | A1 | 7/2006 | Wu et al. |
| 2006/0245978 | A1 | 11/2006 | Prins |
| 2006/0263241 | A1 | 11/2006 | Beebe et al. |
| 2009/0264550 | A1 | 10/2009 | Rayner |
| 2010/0078077 | A1 | 4/2010 | Ismagilov et al. |
| 2010/0093109 | A1 | 4/2010 | Pugia et al. |
| 2010/0116343 | A1 | 5/2010 | Weibel et al. |
| 2010/0163109 | A1 | 7/2010 | Fraden et al. |
| 2012/0024708 | A1 | 2/2012 | Chiou et al. |
| 2013/0037115 | A1 | 2/2013 | Beebe et al. |
| 2014/0125718 | A1 | 5/2014 | Morrision et al. |
| 2015/0011438 | A1 | 1/2015 | Chien et al. |
| 2015/0034163 | A1* | 2/2015 | Abate ...................... B01F 23/41 |
| | | | 137/888 |
| 2015/0132742 | A1 | 5/2015 | Thuo et al. |
| 2016/0059232 | A1 | 3/2016 | Muelleder et al. |
| 2016/0202101 | A1 | 7/2016 | Sparks |

FOREIGN PATENT DOCUMENTS

| CN | 101262948 A | 9/2008 |
| CN | 103765068 A | 4/2014 |
| CN | 103958050 A | 7/2014 |
| CN | 104004652 A | 8/2014 |
| CN | 104324769 A | 2/2015 |
| CN | 104941706 A | 9/2015 |
| CN | 105142790 A | 12/2015 |
| CN | 105142790 B | 10/2017 |
| DE | 19949735 A1 | 5/2001 |
| EP | 1 525 472 A2 | 4/2005 |
| EP | 1 527 888 A2 | 5/2005 |
| EP | 2 523 004 A1 | 11/2012 |
| EP | 2 937 217 A1 | 10/2015 |
| GB | 2 544 152 A | 5/2017 |
| JP | H07-245467 A | 9/1995 |
| JP | 2009-511083 | 3/2009 |
| JP | 2009-118798 A | 6/2009 |
| JP | 2009-537652 A | 10/2009 |
| JP | 2010-526293 A | 7/2010 |
| JP | 5296054 B2 | 7/2010 |
| JP | 2010-531971 A | 9/2010 |
| JP | 5236667 B2 | 9/2010 |
| WO | WO-2004/011938 A2 | 2/2004 |
| WO | WO-2005/122672 A2 | 12/2005 |
| WO | WO-2006/121667 A2 | 11/2006 |
| WO | WO-2007/136328 A1 | 11/2007 |
| WO | WO-2008/063135 A1 | 5/2008 |
| WO | WO-2008/127818 A2 | 10/2008 |
| WO | WO-2009/063135 A1 | 5/2009 |
| WO | WO-2011/097677 A1 | 8/2011 |
| WO | WO-2014/117088 A1 | 7/2014 |
| WO | WO-2014/172740 A1 | 10/2014 |

OTHER PUBLICATIONS

Berthier, et al., "Flow rate analysis of a surface tension driven passive micropump," Lab on a Chip, 2007, pp. 1475-1478, vol. 7, Issue 11.
Bonn, et al., "Wetting and spreading," Reviews of Modern Physics, Apr.-Jun. 2009, pp. 739-805, vol. 81.
C.V. Boys, "Soap Bubbles, Their colours and the forces which mould them," 1890, 12th Thousand Enlarged Edition, 202 pages.
Cate, et al., "Recent Developments in Paper-Based Microfluidic Devices," Analytical Chemistry, 2015, pp. 19-41, vol. 87.
Fletcher, et al., "Theoretical considerations of chemical reactions in micro-reactors operating under electroosmotic and electrophoretic control," The Analyst, 1999, pp. 1273-1282, vol. 124.
Gau, et al., "Liquid Morphologies on Structured Surfaces: From Microchannels to Microchips," Science, Jan. 1, 1999, pp. 46-50, vol. 283.
Hancock, et al., "Surface-Tension-Driven Gradient Generation in a Fluid Stripe for Bench-Top and Microwell Applications," Small, 2011, pAGES Surface-Tension-Driven Gradient Generation in a Fluid Stripe for Bench-Top and Microwell Applications, 2011, pp. 892-901, vol. 7.
Hartmann, et al., "Non-contact protein microarray fabrication using a procedure based on liquid bridge formation," Analytical and Bioanalytical Chemistry, 2008, pp. 591-598, vol. 393, Issue 2.
International Search Report and Written Opinion in International Application No. PCT/GB2016/053204 mailed on Dec. 14, 2016 (12 pages).
International Search Report and Written Opinion in PCT/GB2017/051065 dated Jul. 27, 2017 (11 pages).
Javadi, et al., "Effect of wetting on capillary pumping in microchannels," Scientific Reports, 2013, pp. 1-6, vol. 3.
Ju, et al., "Backward flow in a surface tension driven micropump," Journal of Micromechanics and Microengineering, 2008, pp. 1-5, vol. 18.
Kolesky, et al., "3D Bioprinting of Vascularized, Heterogeneous Cell-Laden Tissue Constructs," Advanced materials, 2014, pp. 3124-3130, vol. 26.

(56) References Cited

OTHER PUBLICATIONS

Kolesky, et al., "Three-dimensional bioprinting of thick vascularized tissues," PNAS, Mar. 22, 2016, pp. 3179-3184, vol. 113, No. 12.
Lam, et al., "Surface-Tension-Confined Microfluidics," Langmuir, 2002, pp. 948-951, vol. 18, No. 3.
Lee, et al., "Capillary Based Patterning of Cellular Communities in Laterally Open Channels," Analytical Chemistry, Apr. 1, 2010, pp. 2900-2096, vol. 82, No. 7.
Lee, et al., "Wall-less liquid pathways formed with three-dimensional microring arrays," Applied Physics Letters, 2012, pP. 114108-1-114108-4, vol. 101.
Lee, et al., "Wall-Less Microfluidic Channels Using 3-Dimensional Ring Arrays," 16th International Conference on Minaturized Systems for Chemistry and Life Sciences, Oct. 28-Nov. 1, 2012, p. 296.
Liberski, et al., "Inkjet fabrication of polymer microarrays and grids—solving the evaporation problem," ChemComm, 2009, pp. 334-336.
Liberski, et al., "'Once Cell-One Well': A New Approach to Inkjet Printing Single Cell Microarrays," ACS Combinatorial Science, 2011, pp. 190-195, vol. 13, Issue 190.
Liu, et al., "A generalized formula for inertial lift on a sphere in microchannels," Lab on a Chip, 2016, pp. 884-892, vol. 16.
Macleod, et al., "A Growing-Drop Technique for Measuring Dynamic Interfacial Tension," Journal of Colloids and Interface Science, Oct. 1993, pp. 435-448, vol. 160.
Memic, et al., "Research Highlights," Lab on a Chip, 2013, pp. 4157-4159, vol. 13.
Oliveira, et al., "Two-Dimensional Open Microfluidic Devices by Tuning the Wettability on Patterned Superhydrophobic Polymeric Surface," Applied Physics Express, 2010, 4 pages, vol. 3.
Parekh, et al., "Miniaturisation for chemistry, physics, biology, materials science and bioengineering," Lab on a Chip, 2016, pp. 1812-1820, vol. 16.
Rahmanian, et al., "Pen microfluidics: rapid desktop manufacturing of sealed thermoplastic microchannels," Lab Chip, 2013, pp. 1102-1108, vol. 13.
Schutzius, et al., "Surface tension confined (STC) tracks for capillary-driven transport of low surface tension liquids," Lab on a Chip, 2012, pp. 5237-5242, vol. 12.
Setu, et al., "Superconfinement tailors fluid flow at microscales," Nature Communications, 2015, pp. 1-8, vol. 6.
Shemesh, et al., "Stationary nanoliter droplet array with a substrate of choice for single adherent/nonadherent cell incubation and analysis," PNAS, Aug. 5, 2014, pp. 11293-11298, vol. 111, No. 31.
Sousa, et al., "Patterned superhydrophobic paper for microfluidic devices obtained by writing and printing," Cellulose, 2013, pp. 2185-2190, vol. 20.
Speth, et al., "Capillary instability on a hydrophilic stripe," New Journal of Physics, 2009, 15 pages, vol. 11.
Straub, "The Role of Surface Tension for Two-Phase Heat and Mass Transfer in the Absence of Gravity," Experimental Thermal and Fluid Science, 1994, pp. 253-273, vol. 9.
Sugden, "The Determination of Surface Tension from the Maximum Pressure in Bubbles," Journal of Chem. Soc. Trans., 1922, pp. 858-866.
Sun, et al., "A novel picoliter droplet array for parallel real-time polymerase chain reaction based on double-inkjet printing," Lab on a Chip, 2014, pp. 3603-3610, vol. 14.
Sun, et al., "Droplet-in-oil array for picoliter-scale analysis based on sequential inkjet printing," Lab on a Chip, 2015, pp. 2429-2436, vol. 15.
Tan, et al., "Microfluidic mixing in a Y-junction open channel," AIP Advances, 2012, pp. 032160-1-032160-11, vol. 2.
Tan, et al., "Stability of flowing open fluidic channels," AIP Advances, 2013, pp. 022121-1-022121- 12, vol. 3.
Tseng, et al., "Research highlights: printing the future of microfabrication," Lab on a Chip, 2014, pp. 1491-1495, vol. 14.
Walker, et al., "A passive pumping method for microfluidic devices," Lab on a Chip, 2001, pp. 131-134, vol. 2.
Washizu, "Electrostatic Actuation of Liquid Droplets for Microreactor Applications," IEEE Transactions on Industry Applications, Jul./Aug. 1998, pp. 732-737, vol. 34, No. 4.
You, et al., "Surface-Tension-Confined Microfluidics and Their Applications," ChemPhysChem, 2013, pp. 471-481, vol. 14.
Zhu, et al., "Nanoliter-Scale Protein Crystallization and Screening with a Microfluidic Droplet Robot," Scientific Reports, 2014, pp. 1-9, vol. 4.
Zhu, et al., "Printing 2-Dimentional Droplet Array for Single-Cell Reverse Transcription Quantitative PCR Assay with a Microfluidic Robot," Scientific Reports, 2015, pp. 1-7, vol. 5.
Final Office Action dated Oct. 22, 2020, from U.S. Appl. No. 15/768,323.
Non-Final Office Action dated Sep. 24, 2020, from U.S. Appl. No. 16/326,134.
US Final Office Action dated Jun. 17, 2022, from U.S. Appl. No. 15/768,323.
US Non-Final Office Action dated Nov. 9, 2021, from U.S. Appl. No. 15/768,323.
Non-Final Office Action dated Apr. 28, 2020, from U.S. Appl. No. 15/768,323.
Notice of Allowance dated Dec. 23, 2020, from U.S. Appl. No. 16/326,134.

\* cited by examiner

METHODS AND APPARATUS FOR MANUFACTURING A MICROFLUIDIC ARRANGEMENT, AND A MICROFLUIDIC ARRANGEMENT

CROSS REFERENCE TO RELATED APPLICATIONS

The present application is a U.S. National Stage of International Application No. PCT/GB2017/051065 filed on Apr. 18, 2017, which claims the benefit of U.K. Patent Application Nos. 1614139.2, 1614146.7, 1614150.9, 1614153.3, 1614157.4 all filed on Aug. 18, 2016 and International Application No. PCT/GB2016/053204 filed on Oct. 14, 2016, the entire disclosures of all of which are incorporated herein by reference in their entireties.

The invention relates to creating a microfluidic arrangement by dividing a body of a first liquid into a plurality of sub-bodies of liquid that are separated from each other by a second liquid and held stably by surface tension. The sub-bodies can be used to provide isolated samples containing material to be investigated, such as living cells or other biological material.

Microwell plates are widely used for studies involving biological material. Miniaturisation of the wells allows large numbers of wells to be provided in the same plate. For example, plates having more than 1000 wells, each having a volume in the region of tens of nanolitres, are known. Further miniaturisation is difficult, however, due to the intrinsic need to provide solid walls that separate the wells from each other. The thickness of these walls reduces the surface area available for the wells. For a typical plate having 1536 wells, for example, the walls would be expected to occupy about 60% of the available surface for current designs. For higher densities the proportion of the surface area made unavailable by the walls will increase further.

A further obstacle to miniaturisation of microwell plates is the difficulty of adding liquids to small wells defined by physical walls. For liquid to be added reliably to a well (i.e. in a way which avoids trapping of air beneath the liquid), a tip needs to be advanced accurately to the bottom of the well without the tip or any liquid attached to the tip touching the walls of the well. If contact is made with the walls before the liquid reaches the bottom of the well it is likely that a meniscus will form with the wall and trap air beneath the liquid. This may mean that liquid cannot reach the bottom of the well.

Microwell plates also lack flexibility because the size of the wells and the number of wells per plate is fixed. Furthermore, biological and chemical compatibility can be limited by the need to use a material that can form the structures corresponding to the wells in an efficient manner. For example, for high density plates it may be necessary to use a material such as polydimethylsiloxane (PDMS), but untreated PDMS has poor biological and chemical compatibility because it teaches toxin and reacts with organic solvents.

EP 1 527 888 A2 discloses an alternative approach in which ink jet printing is used to form an array of closely spaced droplets of growth medium for culture and analysis of biological material. This approach provides more flexibility than a traditional microwell plate but requires sophisticated equipment to perform the printing. Additionally, it is time consuming to add further material to the droplets after the droplets have been formed and there is significant footprint not wetted by the resultant sessile drops as they do not tessellate.

It is an object of the invention to provide an alternative way of creating a microfluidic arrangement that at least partially addresses one or more of the challenges discussed above.

According to an aspect of the invention, there is provided a method of manufacturing a microfluidic arrangement, comprising: providing a continuous body of a first liquid in direct contact with a substrate; providing a second liquid in direct contact with the first liquid and covering the first liquid, such that the first liquid is in direct contact exclusively with the second liquid and the substrate; and forcing the second liquid through the first liquid and into contact with the substrate in selected regions of the substrate in order to divide the continuous body of the first liquid into a plurality of sub-bodies of the first liquid that are separated from each other by the second liquid, wherein: the first liquid is immiscible with the second liquid; and surface tension stably holds the plurality of sub-bodies of the first liquid separated from each other by the second liquid.

The method allows sub-bodies of a liquid to be formed flexibly on a substrate without any mechanical or chemical structures being provided beforehand to define the geometry of the sub-bodies. The shapes and sizes of the sub-bodies are defined by the shapes and sizes of the selected regions of the substrate that the second liquid is forced to contact. As described below, the choice of the selected regions is relatively unrestricted. It is possible to create extremely small sub-bodies, for example of the order of 100 microns or smaller, which would be difficult or impossible to create at reasonable cost using standard microwell plate manufacturing techniques. The sub-bodies can also be positioned much closer to each other than is possible using microwell plates with physical walls. The liquid walls of embodiments of the present disclosure typically have a thickness of 70-120 microns, which allows more than 90% of the surface area of the microfluidic arrangement to be available for containing liquids to be manipulated. Furthermore, there are no solid walls to interfere with adding further liquid to any of the sub-bodies.

In comparison with arrays of droplets deposited by ink jet printing or the like, the method avoids the need for sophisticated printing equipment and can achieve higher space filling efficiency (because the shapes of the sub-bodies do not need to be circular). Materials to be investigated (e.g. cells) and test substances (e.g. drugs) can be added to multiple sub-bodies simultaneously by adding them to the continuous body of the first liquid before it is divided into the sub-bodies. Concentration gradients can be imposed in strips of the first liquid and the strips can be divided into sub-bodies to quickly and easily create multiple samples containing different concentrations of components. The inventors have furthermore found that depositing fluid into the sub-bodies after they have been formed can be achieved more efficiently (merging occurs more quickly) for sub-bodies that do not have a round footprint (e.g. substantially square or rectangular sub-bodies). Without wishing to be bound by theory, it is thought this effect may be influenced by the reduced symmetry of the non-circular sub-bodies and/or by the fact that they can be flatter. Non-circular sub-bodies can be formed easily using methods of the disclosure.

In an embodiment, the forcing of the second liquid through the first liquid is performed by moving a distal tip of a separator member through the first liquid over the selected regions of the substrate; and at least a portion of the distal tip of the separator member has a surface energy density that is lower in respect of contact with the second liquid than in respect of contact with the first liquid.

The surface properties of the separator member allow the second liquid to be dragged through the first liquid quickly and efficiently, allowing the dividing process to be performed reliably and at high speed. The simple approach of moving a separator element through the first liquid can be implemented using relatively inexpensive hardware.

In an embodiment, the continuous body of the first liquid is laterally constrained predominantly by surface tension.

Forming the continuous body in this way is desirable because it means that the first liquid does not have to spread out over the whole surface of the receptacle. This means that the shape can be controlled independently of the shape of the receptacle, which allows more optimal space filling. The continuous body can be arranged to be square or rectangular, for example, which allows an array of square or rectangular sub-bodies to be formed with minimal wastage of the first liquid, even when the receptacle itself is not square or rectangular. Furthermore, the clearance between the continuous body and the lateral walls of the receptacle can reduce the risk of interference between the walls and any elements being used to form the continuous body or to divide the continuous body into sub-bodies. Multiple discrete continuous bodies (e.g. squares or rectangles) can be formed in this way. The inventors have furthermore found that the depth of the first liquid can be higher, without the thickness of the layer being disrupted by the denser second liquid above, when the first liquid is laterally constrained predominantly by surface tension rather than by lateral walls of a receptacle.

In an embodiment, the forcing of the second liquid through the first liquid comprises the following steps in order: dividing the continuous body of the first liquid symmetrically into two sub-bodies of equal volume; and repeatedly dividing each sub-body formed by a preceding dividing step symmetrically into two further sub-bodies of equal volume.

This approach allows multiple sub-bodies of equal volume to be formed accurately and reliably.

In an embodiment, an area of contact between each sub-body and the substrate comprises a sub-body footprint with a sub-body footprint outline; and at least a subset of the sub-body footprint outlines tessellate with respect to each other.

In contrast to prior art methods based on ink jet printing of droplets, embodiments of the present disclosure allow sub-bodies that tessellate with each other to be produced in an efficient manner, thereby achieving high space filling.

In an embodiment, the second liquid is denser than the first liquid.

The method is surprisingly effective using a second liquid that is denser than the first liquid, despite the forces of buoyancy which might be expected to lift the first liquid away from contact with the substrate. Allowing use of a denser second liquid advantageously widens the range of compositions that can be used for the second liquid. Furthermore, the maximum depth of first liquid that can be retained stably in each sub-body without the first liquid spreading laterally over the substrate is increased.

In an embodiment, a material to be investigated is provided in the continuous body of the first liquid, and the division into sub-bodies generates a plurality of isolated samples that each contain a portion of the material to be investigated. In an embodiment, the material to be investigated comprises adherent living cells and at least a portion of the cells are allowed to adhere to the substrate before the continuous body of the first liquid is divided into the sub-bodies. A test substance (e.g. drug) is added to the continuous body of the first liquid after at least a portion of the adherent living cells have adhered to the substrate. The division into the sub-bodies is performed after the test substance has been added to the continuous body of the first liquid.

Thus, a methodology is provided which allows adhered living cells to be treated en masse after they have been allowed to adhere to a substrate and be divided into plural isolated samples later on. This is not possible using prior art approaches and saves considerable time and system complexity, particularly where it is desired to create large numbers of isolated samples and minimum disruption to the cells. It also ensures that cells in each sample have been exposed to very similar conditions, which is difficult to ensure when test substances (e.g. drugs) are added to individual wells or droplets manually, which may impose significant delays between treatment, and physical environments due to inkjet printing or drop-seq method, of different samples. The cells can be placed on the surface without the stresses that would be imposed by passing them through a printing nozzle of an inkjet style printing system. Allowing the cells to adhere before they are cut up provides a better representation of more classical well plate starting conditions for drug screening than alternative approaches in which cells are brought into miniature volumes before they adhere (e.g. via droplet printing). The inventors have furthermore found that cell survival is higher in the sub-bodies formed according to embodiments of the present disclosure in comparison to when the cells were added or present in droplets of the same volume prior to adhesion of the cells.

According to an alternative aspect, there is provided an apparatus for manufacturing a microfluidic arrangement, comprising: an injection system configured to provide a continuous body of a first liquid in direct contact with a substrate by ejecting the first liquid through the distal tip of an injection member while moving the injection member over the substrate to define the shape of the continuous body of the first liquid; a separator system comprising a separator member having a distal tip, the separator system being configured in use to force a second liquid, the second liquid being immiscible with the first liquid, provided in direct contact with the first liquid and covering the first liquid such that the first liquid is in direct contact exclusively with the second liquid and the substrate, through the first liquid and into contact with the substrate in selected regions of the substrate by moving the distal tip of the separator member through the first liquid over the selected regions of the substrate, thereby dividing the continuous body of the first liquid into a plurality of sub-bodies of the first liquid that are separated from each other by the second liquid; and a controller configured to control movement of the injection member over the substrate during the forming of the continuous body of the first liquid and to control movement of the separator member over the substrate during the dividing of the continuous body of the first liquid into the plurality of sub-bodies of the first liquid.

Thus, an apparatus is provided that is capable of performing methods according to the disclosure.

In an embodiment, the injection member and separator member are provided as separate members, allowing optimal properties for the external surfaces of these members to be provided. In an embodiment, at least a portion of the distal tip of the separator member has a surface energy density that is lower in respect of contact with the second liquid than in respect of contact with the first liquid. Preferably, at least a portion of the distal tip of the injection member has a surface energy density that is lower in respect of contact with the first liquid than in respect of contact with the second liquid. The surface properties of the separator member allow the second liquid to follow the movement of the separator member efficiently, thereby displacing the first liquid efficiently. The surface properties of the injection member allow the continuous body of the first liquid to be formed efficiently, even when the continuous body of the first liquid is formed while the second liquid is already present (e.g. by inserting the distal tip through the second liquid to form the continuous body of the first liquid). The surface properties of the injection member also allow the injection member to be used to modify the shape of the first liquid on the substrate after it has been formed (e.g. by spreading the first liquid into new regions on the substrate by dragging the distal tip across the substrate).

Embodiments of the invention will now be described, by way of example only, with reference to the accompanying drawings in which corresponding reference symbols indicate corresponding parts, and in which.

Figure 1:
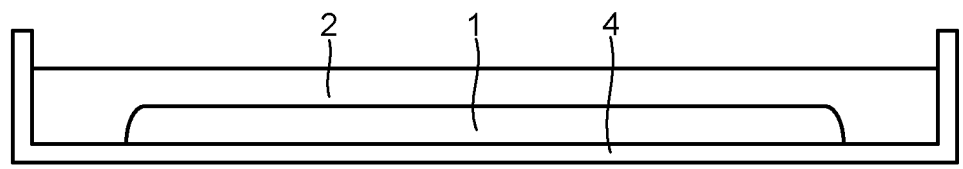
FIG. 1 is a schematic side view of a continuous body of a first liquid on a substrate with a second liquid in direct contact with the first liquid and covering the first liquid.

The figures are provided for explanatory purposes only and are not depicted to scale in order to allow constituent elements to be visualised clearly. In particular, the width of the receptacle providing the substrate relative to the depth of the first and second fluids will in practice be much larger than depicted in the drawings.

Methods are provided for conveniently and flexibly manufacturing a microfluidic arrangement.

As depicted schematically in FIG. 1, a continuous body of a first liquid 1 is provided. The first liquid 1 is in direct contact with a substrate 4. In an embodiment the first liquid 1 comprises an aqueous solution but other compositions are possible. A second liquid 2 is provided in direct contact with the first liquid 1. The second liquid 2 is immiscible with the first liquid. In an embodiment, the continuous body of the first liquid 1 is formed on the substrate 4 before the second liquid 2 is brought into contact with the first liquid 1. In other embodiments, the continuous body of the first liquid 1 is formed after the second liquid 2 is provided (e.g. by injecting the first liquid 1 through the first liquid 2). In embodiments in which the microfluidic arrangement is to be used for testing samples of biological material, the continuous body of the first liquid 1 will normally be formed before the second liquid 2 is provided. The second liquid 2 covers the first liquid 1. The first liquid 1 is thus completely surrounded and in direct contact exclusively with a combination of the second liquid 2 and the substrate 4. At this point in the method the first liquid 1 is not in contact with anything other than the second liquid 2 and the substrate 4. Typically, the substrate 4 will be unpatterned (neither mechanically nor chemically), at least in the region in contact with (typically underneath) the continuous body of the first liquid 1. In an embodiment, the continuous body of the first liquid 1 is in direct contact exclusively with a substantially planar portion of the substrate 4 and the second liquid 2.

As depicted in FIGS. 2-5, in a subsequent step the second liquid 2 is forced through the first liquid 1 and into contact with the substrate 4 in selected regions 5 of the substrate 4. The second liquid 2 thus displaces the first liquid 1, contacting the substrate 4 in the selected regions 5 instead of the first liquid 1. The effect of bringing the second liquid 2 into contact with the substrate 4 in the selected regions 5 of the substrate 4 is to divide the continuous body of the first liquid 1 into a plurality of sub-bodies that are separated from each other by the second liquid 2. Surface tension stably holds the plurality of sub-bodies of the first liquid 1 separated from each other by the second liquid 2.

The method allows sub-bodies of the first liquid 1 to be formed flexibly on the substrate 4 without any mechanical or chemical structures being created beforehand to define the geometry of the sub-bodies.

The particular compositions of the first liquid 1, second liquid 2 and substrate 4 are not particularly limited. However, it is desirable that the first liquid 1 and the second liquid 2 can wet the substrate 4 sufficiently for the method to operate efficiently. In an embodiment, the first liquid 1, second liquid 2 and substrate 4 are selected such that an equilibrium contact angle of a droplet of the first liquid 1 on the substrate 4 in air and an equilibrium contact angle of a droplet of the second liquid 2 on the substrate 4 in air would both be less than 90 degrees. In an embodiment, the first liquid 1 comprises an aqueous solution. In this case the substrate 4 could be described as hydrophilic. In an embodiment, the second liquid 2 comprises a fluorocarbon such as FC40 (described in further detail below). In this case the substrate 4 could be described as fluorophilic. In the case where the first liquid 1 is an aqueous solution and the second liquid 2 is a fluorocarbon, the substrate 4 could therefore be described as being both hydrophilic and fluorophilic.

In an embodiment, the forcing of the second liquid 2 through the first liquid 1 is performed by moving a distal tip of a separator member 6 through the first liquid 1 over the selected regions 5 of the substrate 4. The distal tip displaces the first liquid 1 and allows the second liquid 2 to move into the volume previously occupied by the first liquid 1. The second liquid 2 is thereby forced through the first liquid 1. In an embodiment, this process is facilitated by arranging for at least a portion of the distal tip of the separator member 6 to have a surface energy density that is lower in respect of contact with the second liquid 2 than in respect of contact with the first liquid 1. In this way, it is energetically more favourable for the second liquid to flow into the region behind the moving distal tip and thereby displace the first liquid efficiently. Preferably the substrate 4 is also configured so that it is energetically favourable for the second liquid 2 to wet the substrate 4 and thereby remain in contact with the substrate 4 in the selected regions 5 of the substrate 4 and stably hold the first liquid 1 in the separate sub-bodies.

Figure 2:
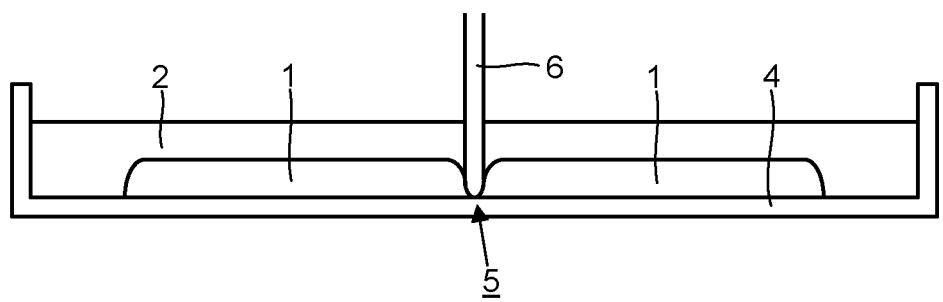
FIG. 2 is a schematic side view of the arrangement of FIG. 1 during dividing of the continuous body of the first liquid using a separator member.
Figure 3:
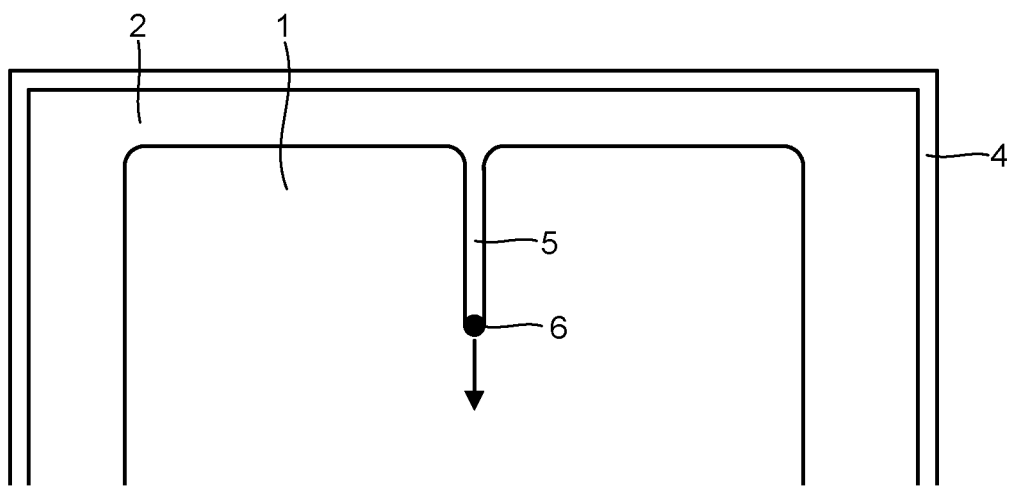
FIG. 3 is a schematic top view of the arrangement of FIG. 2.
Figure 4:
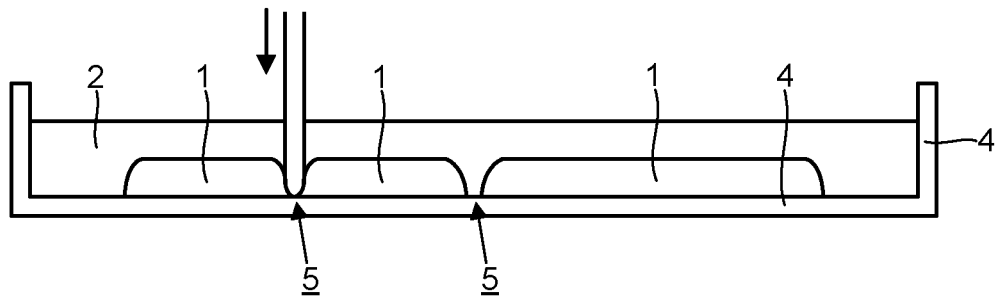
FIG. 4 is a schematic side view showing a subsequent step of further dividing a sub-body.
Figure 5:
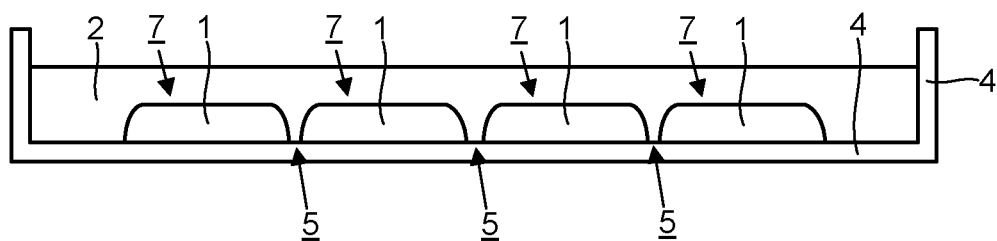
FIG. 5 is a schematic side view showing sub-bodies formed using the methods depicted in FIGS. 3 and 4.

FIGS. 2-5 illustrate an embodiment of this type. FIGS. 2 and 3 depicts movement of a distal tip of a separator member 6 through the first liquid 1 in a horizontal direction, parallel to a plane of the substrate 4 in contact with (typically underneath) the first liquid 1. In FIG. 2, the movement is into the page. In FIG. 3, the movement is downwards. In an embodiment, the distal tip is maintained in contact with the substrate 4 while the distal tip is being moved through the first liquid 1. The distal tip may thus be dragged or drawn along the surface of the substrate 4, like a pencil on a piece of paper. The inventors have found that this approach achieves clean division between different sub-bodies of the first liquid 1. In other embodiments a small separation between the distal tip and the substrate 4 could be maintained during at least part of the movement of the distal tip through the first liquid during the dividing process. In such an embodiment a globule of a liquid other than the first liquid (e.g. the second liquid 2) could be held at the distal tip to ensure that the first liquid 1 is displaced reliably away from the selected regions 5 of the substrate 4. When completed, the process of FIGS. 2 and 3 will result in the continuous body of the first liquid 1 of FIG. 1 being divided into two sub-bodies. The process can be repeated and/or performed in parallel using multiple separator members to create the desired number and size of individual sub-bodies 7 (depicted schematically in FIG. 5). FIG. 4 schematically shows dividing of one of the sub-bodies created in the step of FIGS. 2 and 3 into a further two sub-bodies. FIG. 5 depicts the result of repeating the step of FIG. 4 for the other sub-body created in the step of FIGS. 2 and 3. By repeating the process in the orthogonal direction it is clear that 16 square sub-bodies 7 could be provided. In practice, many 100s or 1000s of sub-bodies 7 could be provided in this manner. The inventors have demonstrated for example that the approach can be used routinely to obtain a square array of sub-bodies having a pitch of less than 100 microns. This is considerably smaller than would be possible using standard microwell plate manufacturing techniques.

Figure 6:
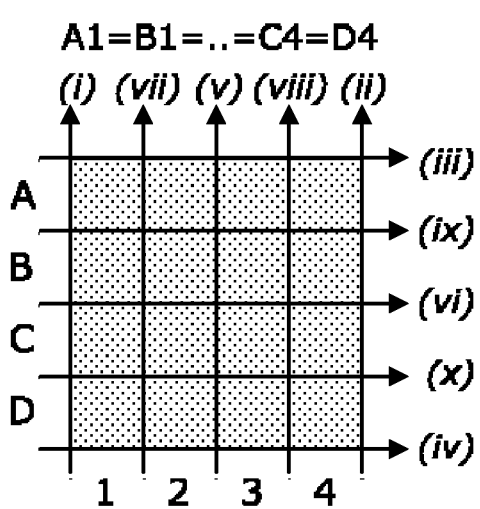
FIG. 6 depicts a dividing scheme resulting in sub-bodies of equal volume.

In an embodiment, a sequence of the dividing process is selected to control the relative volumes of the sub-bodies 7 formed. In an embodiment, as depicted in FIG. 2-6, the forcing of the second liquid 2 through the first liquid 1 comprises the following steps in order: dividing the continuous body of the first liquid 1 symmetrically into two sub-bodies of equal volume; and repeatedly dividing each sub-body formed by a preceding dividing step symmetrically into two further sub-bodies of equal volume. The symmetrical division may comprise division along a line of mirror symmetry of the body or sub-body being divided. FIG. 6 depicts an example sequence. The roman numerals depict the order of a sequence of straight line trajectories of a distal tip of a separator member 6 through the first liquid 1 over the selected regions 5 of the substrate 4 (in this case, straight lines). The trajectories (i)-(iv) first isolate a square initial continuous body of the first liquid 1. Subsequent trajectories (v)-(x) then progressively divide the continuous body and sub-bodies formed therefrom symmetrically into equal volumes until an array of 16 sub-bodies is provided. The symmetrical division at each stage ensures that each and every sub-body has the same volume (thus, A1=B1= . . . C4=D4). An array of any number may be created.

Figure 7:
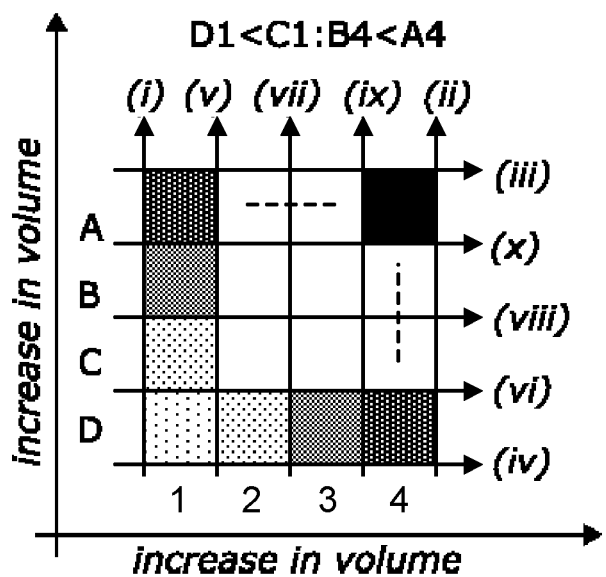
FIG. 7 depicts a dividing scheme for controllably providing sub-bodies of different volumes.

FIG. 7 depicts an alternative dividing scheme for controllably providing sub-bodies of progressively increasing volumes. In this case, trajectories (i)-(iv) are again provided for isolating a square initial continuous body of the first liquid 1. The subsequent trajectories (v)-(x) then scan progressively from the lower left corner to the upper right corner, in each case cutting the continuous body or sub-bodies formed therefrom asymmetrically (except for the final two cuts). The result of this process is that the first liquid is gradually pushed upwards and to the right, leading to a progressive increase in the relative volumes of the sub-bodies (i.e. a progressive increase in their depths) upwards and to the right. This occurs due to a net movement of the first liquid away from the cutting line due to the formation of a curved edge (non-uniform depth) of first liquid 1 along the cutting line. Thus, for each cut there will be a net movement of liquid into the larger of the two sub-bodies formed by the cut.

In an embodiment, an area of contact between each sub-body 7 and the substrate 4 comprises a sub-body footprint with a sub-body footprint outline. At least a subset of the sub-body footprint outlines each comprise at least one straight line portion. This can be achieved for example by forming the sub-bodies using straight line cuts such as those described above with reference to FIGS. 2-7. The array of sub-bodies 7 formed in this manner is therefore fundamentally different to alternative techniques involving deposition of droplets onto the surface of a substrate (where the droplets would have a curved outline). A higher level of space filling is therefore made possible. In an embodiment, at least a subset of the sub-body footprint outlines tessellate with respect to each other. For example, the sub-body footprints may comprise squares, rectangles or parallelograms. All of these four sided shapes can be formed efficiently by performing straight line cuts such as those discussed above with reference to FIGS. 2-7.

In an embodiment, the second liquid 2 is denser than the first liquid 1. The inventors have found that despite the buoyancy forces imposed on the first liquid 1 by the denser second liquid 2 above the first liquid 1, the first liquid 1 surprisingly remains stably in contact with the substrate 4 due to surface tension effects between the first liquid 1 and the substrate 4. Allowing use of a denser second liquid 2 is advantageous because it widens the range of compositions that are possible for the second liquid 2. For example, in a case where the first liquid 1 is an aqueous solution, a fluorocarbon such as FC40 can be used, which provides a high enough permeability to allow exchange of vital gases between cells in the sub-bodies 7 and the surrounding atmosphere through the layer of the second liquid 2. FC40 is a transparent fully fluorinated liquid of density 1.8555 g/ml that is widely used in droplet based microfluidics. Using a second liquid 2 that is denser than the first liquid 1 is also advantageous because it increases the maximum depth of first liquid 1 that can be retained stably in each sub-body 7 without the first liquid 1 spreading laterally over the substrate 4. This is because the weight of the first liquid 1 would tend to force the sub-body 7 downwards and therefore outwards and this effect is counteracted by buoyancy.

Figure 8:
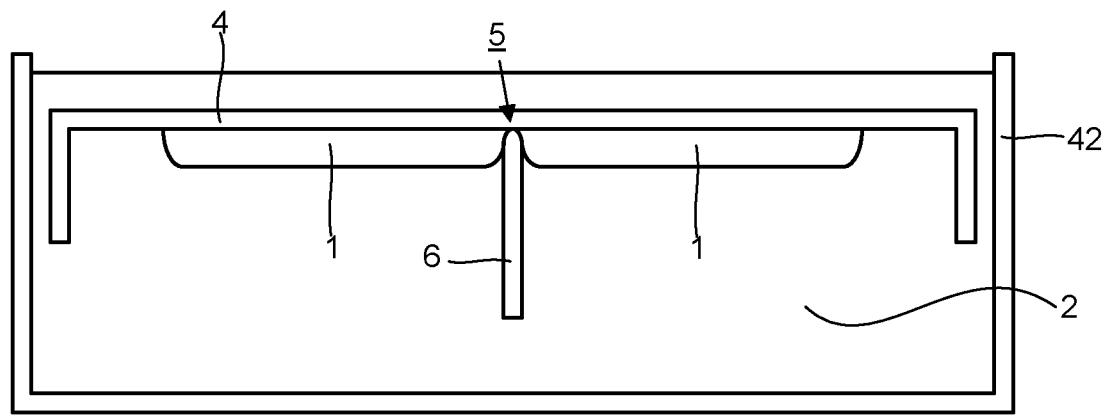
FIG. 8 depicts dividing of a continuous body of the first liquid while the continuous body is held upside down.

In the embodiments discussed above the microfluidic arrangement is formed on an upper surface of a substrate 4. In other embodiments, as depicted in FIG. 8, the microfluidic arrangement can be formed on a lower surface of the surface 4. The dividing of the continuous body of the first liquid 1 can thus be performed with the substrate 4 inverted relative to the arrangement of FIG. 2. In this case, surface tension can hold the first liquid 1 in contact with the substrate 4. The substrate and first liquid 1 can then be immersed in a bath 42 containing the second liquid 2 while the continuous body of the first liquid 1 is divided into sub-bodies using the separator member 6. The subsequent steps described above with reference to FIGS. 2-5 could be performed starting from the arrangement of FIG. 8. This approach may be convenient where the microfluidic arrangement is to be used for the formation of 3D cell culture spheroids for example.

In an embodiment, the continuous body of the first liquid 1 is laterally constrained predominantly by surface tension. For example, the continuous body of the first liquid 1 may be provided only in a selected region on the substrate 4 rather than extending all the way to a lateral wall (e.g. where the substrate 4 is the bottom surface of a receptacle comprising lateral walls, as depicted in FIG. 1). The continuous body is thus not laterally constrained by a lateral wall. This arrangement is particularly desirable where the second liquid 2 is denser than the first liquid 1 because it provides greater resistance against disruptions to the uniformity of thickness of the continuous body of the first liquid 1 due to downward forces on the first liquid 1 from the second liquid 2. The inventors have found that the depth of the first liquid 1 can as a consequence be higher when the first liquid 1 is laterally constrained predominantly by surface tension than when this is not the case. Providing an increased depth of the first liquid 1 is desirable because it allows larger sub-body volumes for a given spatial density of sub-bodies on the substrate. When the sub-bodies are used for culturing cells, for example, the cells may therefore be provided with higher amounts of the required materials, allowing the cells to survive longer and/or under more uniform conditions before further action needs to be taken.

Figure 9:
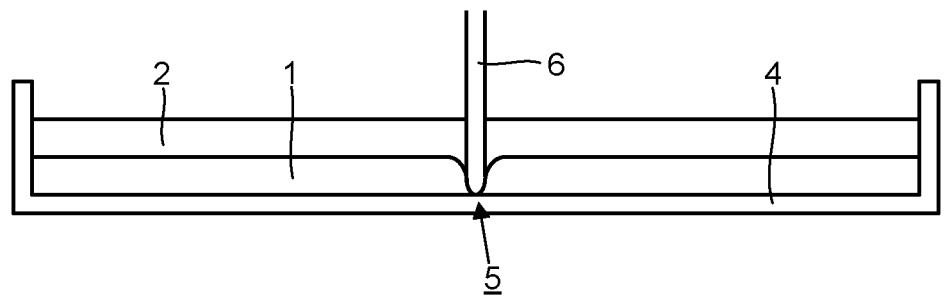
FIG. 9 depicts dividing of a continuous body of the first liquid in a case where the continuous body extends to lateral walls of a receptacle.

In other embodiments, as depicted schematically in FIG. 9, the continuous body of the first liquid may be allowed to extend to the lateral walls of a receptacle providing the substrate 4. A thin film of the first liquid 1 may conveniently be formed in this way by providing a relatively deep layer of the first liquid 1 filling the bottom of the receptacle and then removing (e.g. by pipetting) the first liquid 1 to leave a thin film of the first liquid 1. The arrangement of FIG. 9 corresponds to that of FIG. 2 except for the extension of the continuous body of the first liquid 1 to the lateral walls. The subsequent steps described above with reference to FIGS. 2-5 could be performed starting from the arrangement of FIG. 9.

Figure 10:
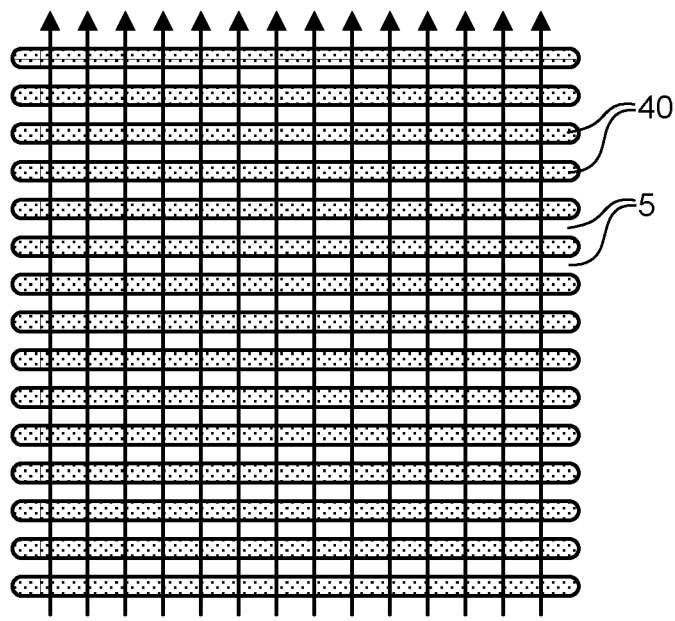
FIG. 10 depicts a dividing scheme in which a continuous body of the first liquid is divided into parallel elongate strips in a first step, wherein each strip is subsequently divided into a plurality of sub-bodies.

In an embodiment, the continuous body of the first liquid 1 is divided into a plurality of elongate strips 40 in an initial step of dividing the continuous body of the first liquid 1 into sub-bodies. In an embodiment, the elongate strips 40 are parallel to each other. An example of such an arrangement is depicted in FIG. 10. The arrangement could be formed for example by moving a separator member 6 along a series of parallel horizontal trajectories to define the selected regions 5 which are to be in contact with the second liquid 2. In a subsequent step, a substance is added to one or more localized regions (e.g. lateral ends) of one or more of the elongate strips 40. The substance migrates (e.g. by diffusion and/or advection) along each elongate strip 40, thereby creating a concentration gradient along the elongate strip 40. In a subsequent step the elongate strips are divided into a plurality of sub-bodies, thereby quickly and easily creating sets of sub-bodies having different concentrations of a selected substance within them. In the particular example of FIG. 10, the division of the elongate strips 40 into the plurality of sub-bodies is performed by moving a separator member 6 along the trajectories marked by solid line arrows in FIG. 10.

Figure 11:
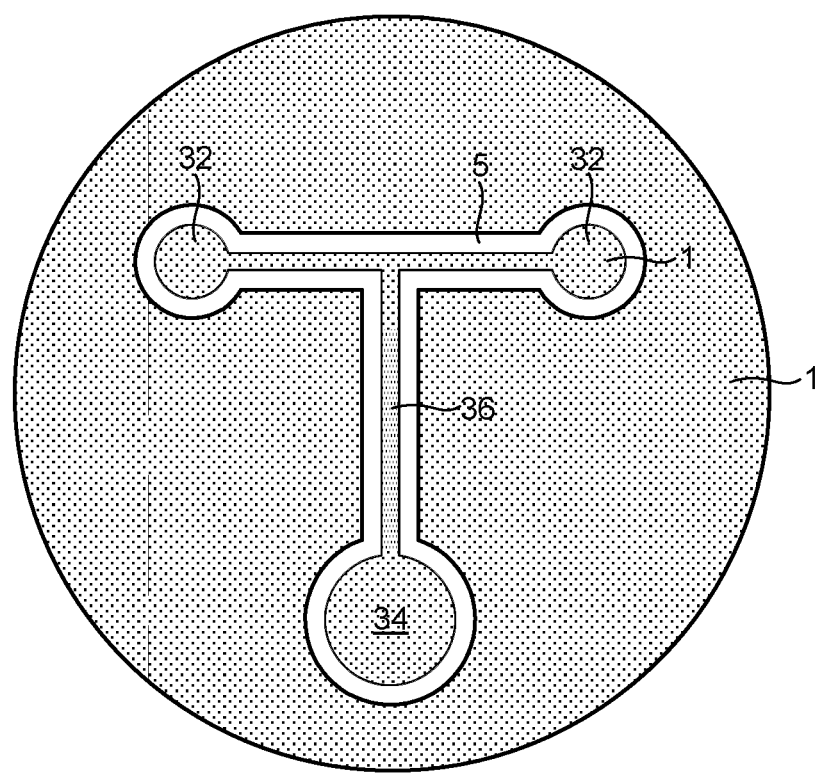
FIG. 11 depicts a dividing scheme in which a continuous body of the first liquid is divided to form at least one sub-body comprising a conduit connected to at least one reservoir.

In an embodiment, more complex shapes can be formed by the dividing of the continuous body of the first liquid 1 into sub-bodies. In one example, as depicted in FIG. 11, the continuous body of the first liquid 1 is divided so that at least one sub-body is formed that comprises at least one conduit 36 connected to at least one reservoir 32, 34. The conduit 36 and reservoir 32, 34 may be configured so that in use a liquid can be driven through the conduit 36 to or from the reservoir 32, 34. The conduit 36 will typically have an elongate form when viewed perpendicularly to the substrate 4. The reservoirs 32, 34 will typically be circular or at least have a lateral dimension that is larger than a width of the conduit 36.

In the particular example shown, a T-shaped conduit 36 is provided that connects two source reservoirs 32 and 34 to a sink reservoir 34. Flow is driven in use, e.g. by Laplace pressure, hydrostatic pressure and/or pumping of material into the reservoirs 32, from the source reservoirs 32 to the sink reservoir 34.

In embodiments of the disclosure the continuous body of the first liquid 1 is formed by depositing the first liquid 1 onto the substrate 4 by ejecting the first liquid 1 from a distal tip while moving the distal tip over the substrate 4 to define the shape of the continuous body of the first liquid. This approach may be used for example when forming a continuous body of the first liquid 1 that is laterally constrained predominantly by surface tension (rather than by walls). FIGS. 12-15 depict two possible implementations.

Figure 12:
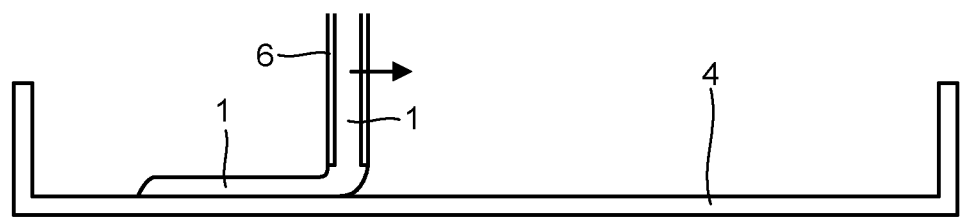
FIGS. 12 and 13 depict use of a separator member to form the continuous body of the first liquid and, in a separate step, to divide the continuous body of the first liquid into sub-bodies.
Figure 13:
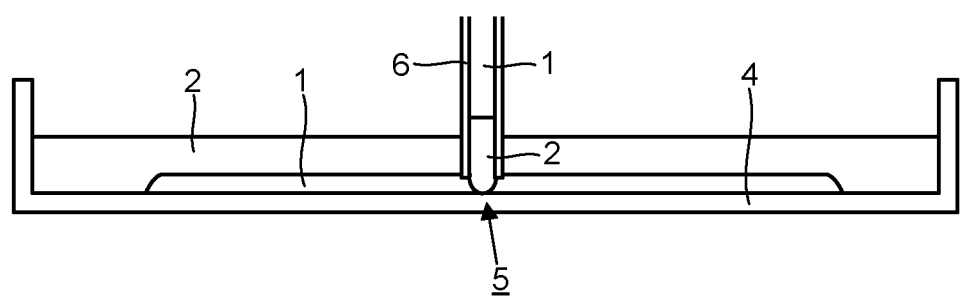

As depicted in FIGS. 12 and 13, in one embodiment the continuous body of the first liquid 1 is provided by ejecting the first liquid 1 through the distal tip of the separator member 6 while moving the separator member 6 over the substrate to define the shape of the continuous body of the first liquid 1. Thus, the same member (the separator member 6) that is later used to divide the continuous body into sub-bodies is also used to form the continuous body in the first place. In FIG. 12, a separator member 6 configured for this purpose is depicted. The separator member 6 comprises an internal lumen. The first liquid 1 can be pumped from a reservoir (not shown) through the internal lumen of the separator member 6 and out of the distal tip of the separator member 6 onto the substrate 4. The distal tip is moved over the substrate 4 to define where the first liquid 1 ends up being positioned on the substrate 4. FIG. 12 schematically depicts such movement from the left to the right in the plane of the page. Surface tension limits lateral spreading of the first liquid 1 over the substrate 4. The continuous body of the first liquid 1 can thus be formed in a wide variety of shapes and sizes. FIG. 13 depicts subsequent use of the separator member 6 to divide the continuous body formed using the process depicted in FIG. 12. In the particular example shown, the division is being performed by moving the separator member through the first liquid 1 into the plane of the page (as in FIG. 2). In this dual use case, it is desirable to avoid any of the first liquid 1 being present near the distal tip of the separator member 6 while the separator member 6 is being used to divide the continuous body of the first liquid 1 into the sub-bodies of the first liquid 1. If any of the first liquid 1 were present near the distal tip, the dividing process could be compromised, thereby reducing reliability. In an embodiment, as depicted in FIG. 13, this risk is reduced or avoided by sucking a portion of the second liquid 2 into the distal tip of the separator member 6 prior to using the separator member 6 to divide the continuous body into the sub-bodies. The second liquid 2 displaces upwards any of the first liquid 1 that may remain in the internal lumen of the separator member 6 from earlier processing steps. The second liquid 2 may be held in the distal tip of the separator member 6 during the forcing of the second liquid 2 through the first liquid 1 using the distal tip of the separator member 6.

Figure 14:
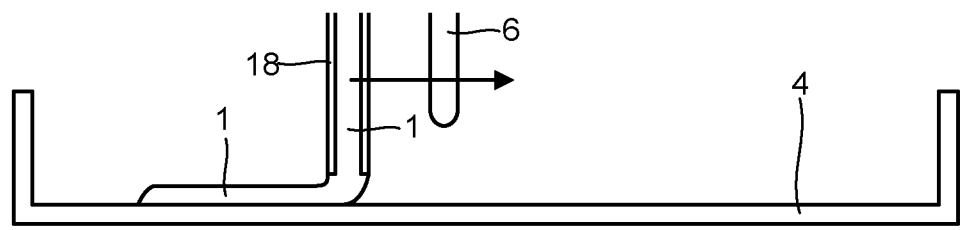
FIGS. 14 and 15 depict use of an injection member to form the continuous body of the first liquid and a separator member, separate from the injection member, to divide the continuous body of the first liquid into sub-bodies.
Figure 15:
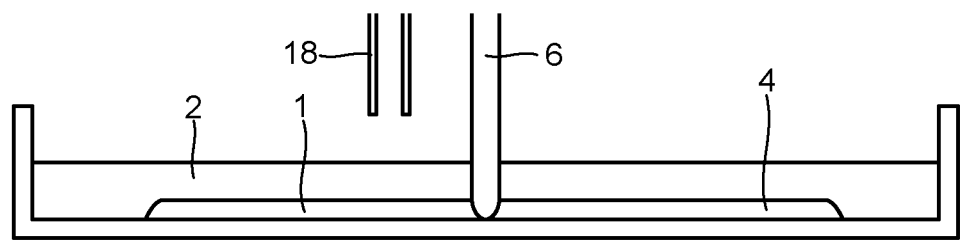

As depicted in FIG. 14-15, in an alternative embodiment the continuous body of the first liquid 1 is provided by ejecting the first liquid 1 through the distal tip of an injection member 18, separate from the separator member 6, while moving the injection member 18 over the substrate 4 to define the shape of the continuous body of the first liquid 1. Thus, different members (an injection member 18 and a separator member 6) are used respectively to form the continuous body initially and, at a later time, to divide the continuous body into the sub-bodies. In this case, the distal tip of the injection member 18 does not necessarily need to provide a surface for which the surface energy density is lower in respect of contact with the second liquid than in respect of contact with the first liquid. Indeed, in some embodiments the injection member 18 is configured so that at least a portion of the distal tip of the injection member 18 has a surface energy density that is lower in respect of contact with the first liquid than in respect of contact with the second liquid. This is convenient because it makes it possible for the injection member 18 to be used to modify the shape of the continuous body or sub-bodies of the first liquid 1 formed at an earlier time, without injection of any further first liquid by the injection member 18. The injection member 18 can be brought into contact with the first liquid and then dragged over the substrate (e.g. while being held a small distance above the substrate 4) in order to extend the continuous body of sub-body in desired ways. The injection member 18 may be used to connect two sub-bodies together that were previously separated from each other, for example. The injection member 18 may be used to connect parts of a conduit together to modify a function of a microfluidic arrangement configured in use to have a flow of liquid driven through the conduit. The injection member 18 can be used to form the continuous body by injecting the first liquid 1 through a layer of the second liquid 2. This would be difficult or impossible to achieve if the first liquid 1 did not wet the distal tip of the injection member 18 to a sufficient extent. In an embodiment, the injection member 18 is surrounded with a sleeve of a material for which the surface energy density is lower in respect of contact with the second liquid than in respect of contact with the first liquid. The sleeve may leave a small region at the distal tip for which the surface energy density is lower in respect of contact with the first liquid than in respect of contact with the second liquid. This arrangement advantageously encourages droplets of the first liquid 1 to form in a controlled way at the distal tip rather than running backwards up the injection member 18. In one embodiment, the first liquid 1 comprises an aqueous solution, the second liquid 2 comprises a fluorocarbon (e.g. FC40), the separator member 6 comprises PTFE and the injection member 18 comprises stainless steel. Stainless steel provides good rigidity, which allows accurate injection of the first liquid 1.

In the particular example of FIGS. 14-15, the injection member 18 and the separator member 6 are mounted on the same processing head 20 (see FIG. 20) and can be moved in unison over the substrate 4. The processing head 20 is configured so that the injection member 18 and the separator member 6 can be selectively advanced and retracted. Thus, as depicted in FIG. 14, the injection member 18 can be advanced and the separator member 6 retracted during formation of the initial continuous body by ejection of the first liquid 1 from the distal tip of the injection member 18. When this is finished and it is desired to divide the continuous body into the sub-bodies, the injection member 18 can be retracted and the separator member 6 advanced. The distal tip of the separator member 6 can then be moved through the first liquid 1 to divide the continuous body of the first liquid 1 into the sub-bodies, as depicted in FIG. 15 (where movement of the distal tip of the separator member 6 is into the page, as in FIGS. 13 and 2).

Figure 16:
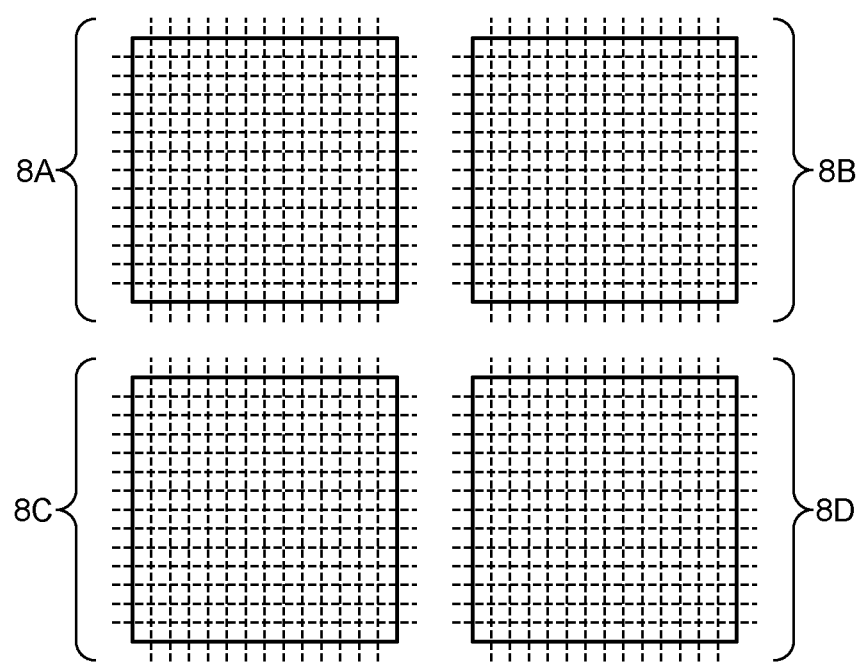
FIG. 16 depicts a scheme for creating multiple sets of sub-bodies of a first liquid having different compositions relative to each other by creating plural continuous bodies of the first liquid and subsequently dividing each of the continuous bodies to create sub-bodies.

In an embodiment, as depicted schematically in FIG. 16, the method is applied to a plurality of continuous bodies of a first liquid 1 formed at different locations on the same substrate 4 by ejecting the first liquid 1 from a distal tip of a member (e.g. an injection member 18 or a separator member 6, as described above) and moving the member over the substrate 4 to define the shape of each of the continuous bodies of the first liquid 1. Each of the continuous bodies of the first liquid 1 is held in place by surface tension. This approach allows multiple initial continuous bodies of the first liquid 1 to be formed having different compositions relative to each other. The different continuous bodies may have different compositions due to deliberate differences in the first liquid 1 as it is ejected from the member or different substances may be added to the different continuous bodies prior to the continuous bodies being divided to create the sub-bodies. In this way, multiple sets of sub-bodies can be created in which the sub-bodies of each set are subjected to the same initial conditions but the sub-bodies of different sets are subjected to different initial conditions. For example, in a case where biological material such as living cells is provided in each of the initial continuous bodies of the first liquid 1, different drugs could be added to two or more of the initial continuous bodies before they are divided into sub-bodies. In the particular example of FIG. 16, four continuous bodies of the first liquid 1 are provided (large squares depicted by solid lines). Each of the four continuous bodies are divided along the broken lines to form separate sets of sub-bodies 8A-D in four square arrays. In an embodiment, the four sets of sub-bodies 8A-D are provided by forming four continuous bodies of identical composition containing living cells. Different drugs are then added to each of the four continuous bodies of identical composition, optionally after the living cells have been allowed to adhere to the substrate 4. The four continuous bodies are divided up to form the four sets of sub-bodies 8A-D and observed at a later time to assess the effect of the different drugs on the cells.

Figure 17:
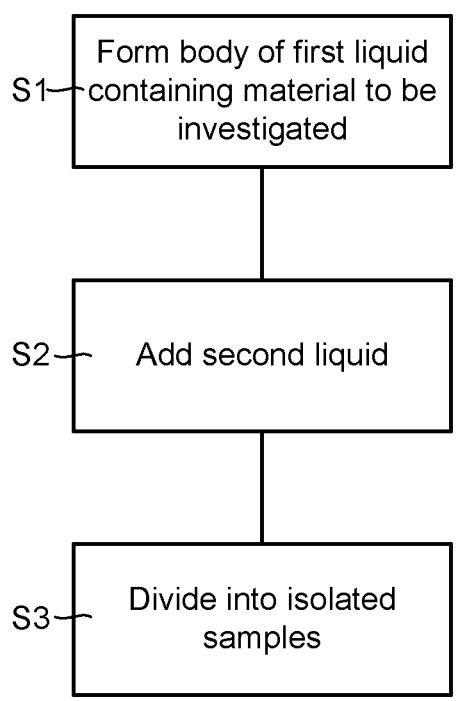
FIG. 17 is a flow chart describing the framework of a method of manufacturing a microfluidic arrangement for testing biological material.

In an embodiment, the manufactured microfluidic arrangement comprises a plurality of isolated samples that are used for investigating a material of interest. The framework of the method is depicted schematically in FIG. 17. In step S1, the continuous body of the first liquid 1 is formed and arranged to contain the material to be investigated. The material to be investigated is provided in the continuous body of the first liquid 1 prior to division of the continuous body to provide the sub-bodies. In the case where the continuous body is formed by ejecting the first liquid 1 from a distal tip while moving the distal tip over the substrate 4, the material to be investigated may be provided in the first liquid 1 while the first liquid 1 is being ejected from the distal tip or may be added afterwards. In step S2, the second liquid is added. In step S3, the continuous body is divided into the plurality of sub-bodies. The process of dividing the continuous body into the sub-bodies generates a plurality of isolated samples that each contain a portion of the material to be investigated without the material to be investigated needing to be added individually to each sample, which would be very time consuming, particularly where large numbers of the sub-bodies are created and/or where the sub-bodies are very small.

In an embodiment, the material to be investigated comprises biological material. In an embodiment, the biological material comprises adherent living cells. Methods of embodiments of the present disclosure are particularly advantageous in this context because they allow adhered living cells to be treated en masse after they have been allowed to adhere to a substrate 4, and divided into plural isolated samples later on. This is not possible using prior art approaches and saves considerable time and system complexity, particularly where it is desired to create large numbers of isolated samples.

Figure 18:
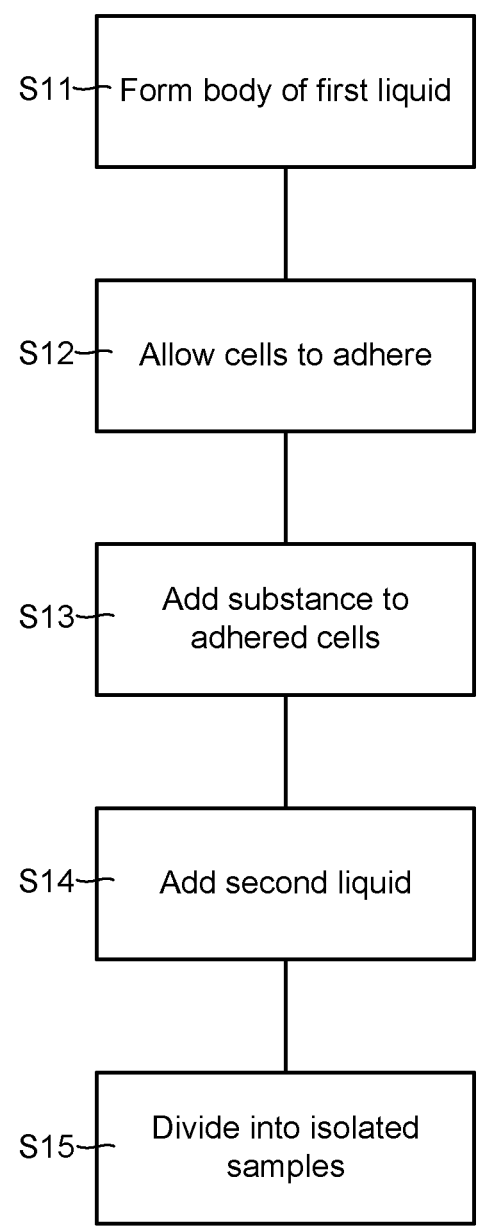
FIG. 18 is a flow chart describing the framework of a method of manufacturing a microfluidic arrangement for testing samples containing adherent living cells and a test substance.

FIG. 18 depicts the framework of a method applicable to handling adherent living cells. In step S11, the continuous body of the first liquid 1 is formed and arranged to contain the adherent living cells. In the case where the continuous body is formed by ejecting the first liquid 1 from a distal tip while moving the distal tip over the substrate 4, the adherent living cells may be provided in the first liquid 1 while the first liquid 1 is being ejected from the distal tip or may be added afterwards. In step S12, at least a portion of the adherent living cells, optionally a majority of the adherent livings cells, are allowed to adhere to the substrate 4 (this may be achieved for example by leaving the cells overnight in appropriate incubation conditions). When the cells are adhered to the substrate 4 to a desired extent, the first liquid 1, which in this case may comprise suitable growth media, may optionally be poured off to leave a thin film of the first liquid 1 before moving on to step S13. In step S13, a test substance (e.g. a drug) is added to the continuous body of the first liquid 1 (which may be a thin film after the pouring off described above) containing the adhered living cells. An excess of the test substance may be optionally poured off at this stage to leave a thin film of first liquid 1 (containing the adhered cells, remnants of the growth media and the test substance). In step S14, the second liquid 2 is added. In step S15, the continuous body of the first liquid 1 is divided into the plurality of sub-bodies. The process of dividing the continuous body into the sub-bodies generates a plurality of isolated samples that each contain adhered living cells and a test substance that was added after the cells had adhered, without the test substance having needed to be added individually to each sample.

Figure 19:
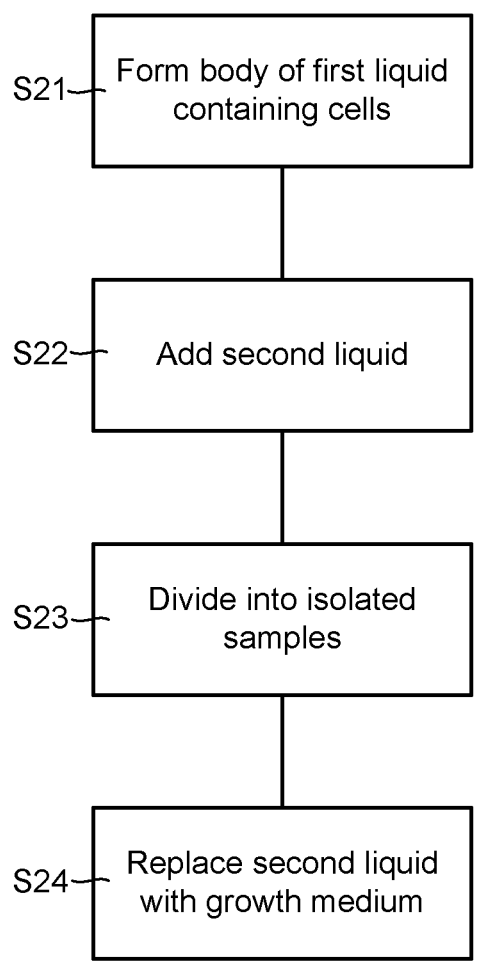
FIG. 19 is a flow chart describing the framework of a method of manufacturing a microfluidic arrangement for growing cell populations in groups.

FIG. 19 depicts the framework of a further method applicable to forming isolated samples containing living cells. In step S21, a continuous body of the first liquid 1 is formed and arranged to contain living cells, optionally adherent living cells. Step S21 may be identical to S11 discussed above. Step S21 may also comprise steps corresponding to either or both of steps S12 and S13 discussed above, so that adherent living cells may be allowed to adhere to the substrate 4 and/or a test substance (e.g. a drug) may be applied to the adhered living cells. In step S22, the second liquid 2 is added. In step S23, the continuous body is divided into the plurality of sub-bodies. In step S24, the second liquid 2 is removed (e.g. by pouring off or syringing). The first liquid 1 may also be removed at this stage. Growth medium is then added to cover the substrate 4. The inventors have found that the dividing lines separating the sub-bodies of the first liquid 1 when they are initially formed underneath the second liquid 2 continue to act as barriers to movement of cells even when the first liquid 1 and second liquid 2 have been removed and replaced by growth medium. Without wishing to be bound by theory, it is believed that the surface of the substrate 4 is modified and/or residues of the first liquid 1 and/or the second liquid 2 are left behind and cause this effect. The result conveniently allows cell populations to be cultured in regions that are isolated from each other, thereby allowing multiple studies of individual populations of cells to be conducted efficiently in parallel. For example, where the sub-bodies initially contained only a single cell, the resulting cell population would all originate from the same single cell.

In an embodiment, the above methods are adapted to implement single cell studies. This can be done for example by providing a concentration of living cells in the initial continuous body of the first liquid 1 that is low enough that the mean occupancy of each sub-body created by dividing the continuous body is less than one living cell. In this way, may sub-bodies will be created that contain one and only one cell. This approach is considerably quicker than alternative approaches requiring individual deposition of cells into separate wells after the wells have been created (e.g. in a microwell plate).

Figure 20:
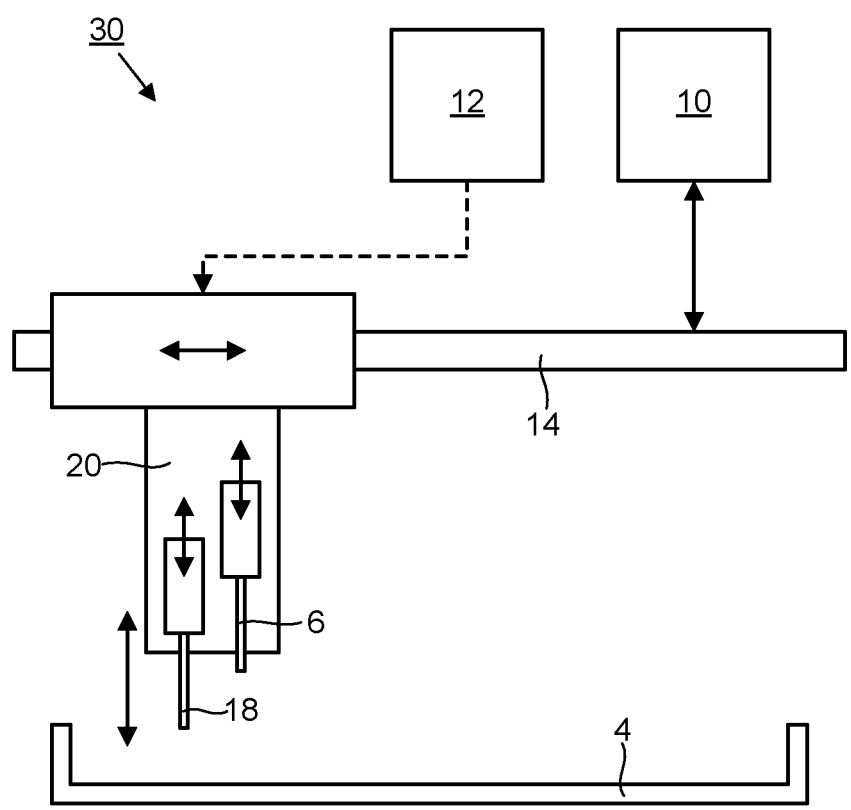
FIG. 20 depicts an apparatus for manufacturing a fluidic arrangement.

FIG. 20 depicts an apparatus 30 for manufacturing a microfluidic arrangement. In the particular example shown, the apparatus 30 is configured to perform the method as described above with reference to FIGS. 14 and 15, but could be modified to perform the method according to any of the other embodiments disclosed. For example, the apparatus 30 could be modified to use a single separator member 6 both to form the initial continuous body 1 of the first liquid 1 and to divide the continuous body into the sub-bodies. Alternatively or additionally, the initial continuous body of the first liquid 1 could be formed using other apparatus elements or simply by filling a lower portion of a receptacle with the first liquid 1 (i.e. such that the first liquid spreads all the way to lateral walls of the receptacle).

The apparatus 30 of FIG. 20 comprises an injection system. The injection system provides the continuous body of the first liquid 1 in direct contact with the substrate 4 by ejecting the first liquid 1 through the distal tip of an injection member 18 while moving the injection member 18 over the substrate 4 to define the shape of the continuous body of the first liquid 1. The injection system comprises the injection member 18 and a pumping system 12. In use, the pumping system 12 will comprise a reservoir containing the first liquid 1, conduits for conveying the first liquid 1 from the reservoir to the internal lumen of the injection member 18, and a mechanism for pumping the first liquid through the internal lumen and out of the distal tip of the injection member 18. In embodiments, the injection system may further be configured to controllably extract the first liquid 1, for example by controllably removing excess first liquid by sucking the liquid back through the injection member 18.

In an embodiment, the apparatus 30 is configured to maintain a small but finite separation between the distal tip of the injection member 18 and the substrate 4 while the injection member 18 is moved over the substrate 4 to form the continuous body of the first liquid 1. This is particularly important where the microfluidic arrangement is to be used for cell-based studies, which would be affected by any scratching or other modification of the surface that might be caused were the injection member 18 to be dragged over the substrate 4 in contact with the substrate 4. Any such modifications could negatively affect optical access and/or cell compatibility. In an embodiment, this is achieved by mounting the injection member 18 slideably in a mounting such that a force from contact with the substrate 4 will cause the injection member 18 to slide within the mounting. Contact between the injection member 18 and the substrate 4 is detected by detecting sliding of the injection member 18 relative to the mounting. When contact is detected, the injection member 18 is pulled back by a small amount (e.g. 20-150 microns) before the injection member 18 is moved over the substrate 4 to form the continuous body of the first liquid 1 (without contacting the substrate 4 during this motion). This approach to controlling separation between the distal tip and the substrate 4 can be implemented cost effectively in comparison to alternatives such as the capacitive/inductive methods used in 3D printers, or optical based sensing techniques. The approach also does not require a conductive surface to be provided.

The apparatus 30 of FIG. 20 further comprises a separator system. The separator system comprises a separator member 6 having a distal tip. The separator system is configured in use to force a second liquid 2 that is immiscible with the first liquid 1 and provided in direct contact with the first liquid 1 and covering the first liquid 1 such that the first liquid 1 is in direct contact exclusively with the second liquid 2 and the substrate 4, through the first liquid 1 and into contact with the substrate 4 in selected regions 5 of the substrate 4 by moving the distal tip of the separator member 6 through the first liquid 1 over the selected regions of the substrate 4, thereby dividing the continuous body of the first liquid 1 into a plurality of sub-bodies of the first liquid 1 that are separated from each other by the second liquid 2. The second liquid 2 may be provided as described above, either before or after the continuous body of the first liquid 1 has been formed (normally after). In an embodiment the apparatus 30 comprises an application system for applying or removing the second liquid 2 (comprising for example a reservoir for holding the second liquid, an output/suction nozzle positionable above the substrate 4, and a pumping/suction mechanism for controllably pumping or sucking the second liquid to/from the reservoir from/to the substrate through the output/suction nozzle). In other embodiments, the second liquid 2 is applied manually.

The apparatus 30 of FIG. 20 further comprises a controller 10. The controller 10 controls movement of the injection member 18 over the substrate 4 during the forming of the continuous body of the first liquid 1. The controller 10 further controls movement of the separator member 6 over the substrate 4 during the dividing of the continuous body of the first liquid 1 into the plurality of sub-bodies of the first liquid 1. In an embodiment, the apparatus 30 comprises a processing head 20 that supports the injection member 18 and the separator member 6. The processing head 20 is configured such that the injection member 18 and the separator member 6 can be selectively advanced and retracted. In an embodiment, the advancement and retraction is controlled by the controller 10, with suitable actuation mechanisms being mounted on the processing head 20. A gantry system 14 is provided to allow the processing head 20 to move as required. In the particular example shown, left-right movement within the page is illustrated but it will be appreciated that the movement can also comprise movement into and out of the page as well as movement towards and away from the substrate 4 (if the movement of the injection member 18 and the separator member 6 provided by the processing head 20 itself is not sufficiently to provide the required upwards and downwards displacement of the injection member 18 and/or separator member 6).

The invention claimed is:

1. A method of manufacturing a microfluidic arrangement, comprising:
    providing a continuous and stationary body of a first liquid in direct contact with a substrate;
    providing a second liquid in direct contact with the continuous and stationary body of the first liquid and covering the continuous and stationary body of the first liquid, such that the first liquid in the continuous and stationary body of the first liquid is in direct contact exclusively with the second liquid and the substrate; and
    forcing the second liquid through the first liquid in the continuous and stationary body of the first liquid and into contact with the substrate in selected regions of the substrate in order to divide the continuous and stationary body of the first liquid into a plurality of stationary sub-bodies of the first liquid that are separated from each other by the second liquid, wherein:
    the first liquid is immiscible with the second liquid;
    surface tension stably holds the plurality of stationary sub-bodies of the first liquid separated from each other by the second liquid; and
    the first liquid in each stationary sub-body is in direct contact with the substrate and covers a cross section of the substrate, and the second liquid completely covers the first liquid in the stationary sub-body and extends outside of the cross section covered by the first liquid to make contact with the substrate and the first liquid.

2. The method of claim 1, wherein:
    the forcing of the second liquid through the first liquid is performed by moving a distal tip of a separator member through the first liquid over the selected regions of the substrate; and
    at least a portion of the distal tip of the separator member has a surface energy density that is lower in respect of contact with the second liquid than in respect of contact with the first liquid.

3. The method of claim 2, wherein:
    the continuous body of the first liquid is provided, before the forcing of the second liquid through the first liquid, by ejecting the first liquid through the distal tip of the separator member while moving the separator member over the substrate to define the shape of the continuous body of the first liquid.

4. The method of claim 3, wherein a portion of the second liquid is sucked into the distal tip of the separator member and held in the distal tip of the separator member during the forcing of the second liquid through the first liquid using the distal tip of the separator member.

5. The method of claim 2, wherein:
the continuous body of the first liquid is provided by ejecting the first liquid through a distal tip of an injection member, separate from the separator member, while moving the injection member over the substrate to define the shape of the continuous and stationary body of the first liquid.

6. The method of claim 1, wherein the continuous and stationary body of the first liquid is formed on the substrate before the second liquid is brought into contact with the first liquid.

7. The method of claim 1, wherein the continuous stationary body of the first liquid is laterally constrained predominantly by surface tension.

8. The method of claim 1, wherein the continuous and stationary body of the first liquid is in direct contact exclusively with a substantially planar portion of the substrate and the second liquid.

9. The method of claim 1, wherein the forcing of the second liquid through the first liquid comprises the following steps in order:
dividing the continuous and stationary body of the first liquid symmetrically into two sub-bodies of equal volume; and
repeatedly dividing each sub-body formed by a preceding dividing step symmetrically into two further sub-bodies of equal volume.

10. The method of claim 1, wherein:
an area of contact between each sub-body and the substrate comprises a sub-body footprint with a sub-body footprint outline; and
at least a subset of the sub-body footprint outlines each comprise at least one straight line portion.

11. The method of claim 1, wherein:
an area of contact between each sub-body and the substrate comprises a sub-body footprint with a sub-body footprint outline; and
at least a subset of the sub-body footprint outlines tessellate with respect to each other.

12. The method of claim 1, wherein the second liquid is denser than the first liquid.

13. The method of claim 1, wherein the first liquid, second liquid and substrate are selected such that an equilibrium contact angle of a droplet of the first liquid on the substrate in air and an equilibrium contact angle of a droplet of the second liquid on the substrate in air would both be less than 90 degrees.

14. The method of claim 1, wherein:
a plurality of the continuous bodies of the first liquid are formed at different locations on the same substrate by ejecting the first liquid from a distal tip of a member and moving the member over the substrate to define the shape of each of the continuous and stationary bodies of the first liquid;
each of the continuous and stationary bodies is initially covered by the second liquid and held in place by surface tension; and
each of the continuous and stationary bodies of the first liquid are subsequently divided into a plurality of sub-bodies that are separated from each other by the second liquid by forcing the second liquid through the first liquid and into contact with the substrate in selected regions of the substrate.

15. The method of claim 1, wherein:
a material to be investigated is provided in the continuous body of the first liquid; and
the division into sub-bodies generates a plurality of isolated samples that each contain a portion of the material to be investigated.

16. The method of claim 15, wherein the material to be investigated comprises biological material.

17. The method of claim 16, wherein the biological material comprises adherent living cells.

18. The method of claim 17, wherein at least a portion of the adherent living cells are allowed to adhere to the substrate before the continuous and stationary body of the first liquid is divided into the sub-bodies.

19. The method of claim 18, wherein:
a test substance is added to the continuous body of the first liquid after at least a portion of the adherent living cells have adhered to the substrate; and
the division into the sub-bodies is performed after the test substance has been added to the continuous body of the first liquid.

20. The method of claim 19, wherein the test substance comprises a drug.

21. The method of claim 15, wherein the second liquid is replaced with growth medium after the division into the sub-bodies.

22. The method of claim 15 wherein the biological material comprises living cells at a concentration such that a mean average occupancy of each sub-body is less than one living cell.

* * * * *